US011432922B2

(12) United States Patent
Detamore et al.

(10) Patent No.: US 11,432,922 B2
(45) Date of Patent: Sep. 6, 2022

(54) BIOMATERIAL BASED ON ALIGNED FIBERS, ARRANGED IN A GRADIENT INTERFACE, WITH MECHANICAL REINFORCEMENT FOR TRACHEAL REGENERATION AND REPAIR

(71) Applicants: The University of Kansas, Lawrence, KS (US); The Children's Mercy Hospital, Kansas City, MO (US)

(72) Inventors: Michael Detamore, Lawrence, KS (US); Lindsey Ott, Lawrence, KS (US); Robert Weatherly, Overland Park, KS (US)

(73) Assignees: The University of Kansas, Lawrence, KS (US); The Children's Mercy Hospital, Kansas City, MO (US)

( * ) Notice: Subject to any disclaimer, the term of this patent is extended or adjusted under 35 U.S.C. 154(b) by 0 days.

(21) Appl. No.: 17/517,027

(22) Filed: Nov. 2, 2021

(65) Prior Publication Data
US 2022/0054255 A1 Feb. 24, 2022

Related U.S. Application Data

(63) Continuation of application No. 16/570,510, filed on Sep. 13, 2019, which is a continuation of application
(Continued)

(51) Int. Cl.
*A61F 2/04* (2013.01)
*A61F 2/06* (2013.01)
(Continued)

(52) U.S. Cl.
CPC ............... *A61F 2/20* (2013.01); *A61F 2/04* (2013.01); *A61L 27/10* (2013.01); *A61L 27/14* (2013.01);
(Continued)

(58) Field of Classification Search
CPC .. A61F 2/2418; A61F 2/20; A61F 2/04; A61F 2/06; A61F 2/07; A61F 2002/072;
(Continued)

(56) References Cited

U.S. PATENT DOCUMENTS

| 5,201,745 A | * | 4/1993 | Tayot | A61F 2/0063 424/428 |
| 6,306,424 B1 | * | 10/2001 | Vyakarnam | A61L 27/56 428/338 |

(Continued)

FOREIGN PATENT DOCUMENTS

| JP | 2001212246 A | 8/2001 |
| WO | 2013025819 A2 | 2/2013 |

OTHER PUBLICATIONS

International Search Report and Written Opinion for PCT/US2012/050974 dated Feb. 28, 2013.
(Continued)

*Primary Examiner* — Seema Mathew
(74) *Attorney, Agent, or Firm* — DLA Piper LLP (US)

(57) ABSTRACT

An implant can include a plurality of polymeric fibers associated together into a fibrous body. The fibrous body is capable of being shaped to fit a tracheal defect and capable of being secured in place by suture or by bioadhesive. The fibrous body can have aligned fibers (e.g., circumferentially aligned) or unaligned fibers. The fibrous body can be electrospun. The fibrous body can have a first characteristic in a first gradient distribution across at least a portion of the fibrous body. The fibrous body can include one or more structural reinforcing members, such as ribbon structural reinforcing members, which can be embedded in the plurality of fibers. The fibrous body can include one or more structural reinforcing members bonded to the fibers with
(Continued)

liquid polymer as an adhesive, the liquid polymer having a substantially similar composition of the fibers.

9 Claims, 9 Drawing Sheets

Related U.S. Application Data

No. 14/239,049, filed as application No. PCT/US2012/050974 on Aug. 15, 2012, now abandoned.

(60) Provisional application No. 61/523,894, filed on Aug. 16, 2011.

(51) Int. Cl.
| | | |
|---|---|---|
| A61F 2/07 | (2013.01) | |
| A61F 2/20 | (2006.01) | |
| A61L 27/10 | (2006.01) | |
| A61L 27/34 | (2006.01) | |
| A61L 27/18 | (2006.01) | |
| A61L 27/14 | (2006.01) | |

(52) U.S. Cl.
CPC .............. *A61L 27/18* (2013.01); *A61L 27/34* (2013.01); *A61F 2002/046* (2013.01); *A61F 2210/0076* (2013.01); *A61F 2250/0018* (2013.01); *A61F 2250/0028* (2013.01); *A61L 2300/414* (2013.01); *A61L 2420/04* (2013.01); *A61L 2420/08* (2013.01); *A61L 2430/22* (2013.01)

(58) Field of Classification Search
CPC ...... A61F 2210/0076; A61F 2250/0023; A61F 2250/0028; A61F 2002/30011; A61F 2002/3092
See application file for complete search history.

(56) References Cited

U.S. PATENT DOCUMENTS

| | | | |
|---|---|---|---|
| 6,743,243 B1 | 6/2004 | Roy et al. | |
| 7,172,765 B2 | 2/2007 | Chu et al. | |
| 7,575,759 B2* | 8/2009 | Murphy .................. | A61L 27/18 424/423 |
| 7,722,671 B1 | 5/2010 | Carlyle et al. | |
| 8,043,480 B2* | 10/2011 | Lahann ................ | D01D 5/0069 264/9 |
| 8,222,166 B2 | 7/2012 | Chu et al. | |
| 8,382,824 B2 | 2/2013 | Weber | |
| 9,737,632 B2* | 8/2017 | Johnson .................. | A61L 27/54 |
| 9,895,354 B2* | 2/2018 | Puleo .................... | A61K 9/146 |
| 10,080,687 B2 | 9/2018 | MacEwan | |
| 10,617,512 B2 | 4/2020 | MacEwan et al. | |
| 10,632,228 B2* | 4/2020 | MacEwan ............... | A61L 27/26 |
| 10,682,444 B2 | 6/2020 | MacEwan | |
| 10,888,409 B2 | 1/2021 | MacEwan et al. | |
| 2002/0020417 A1 | 2/2002 | Nikolchev et al. | |
| 2002/0090725 A1* | 7/2002 | Simpson .............. | D01D 5/0038 623/23.72 |
| 2002/0120348 A1 | 8/2002 | Melican et al. | |
| 2002/0173213 A1* | 11/2002 | Chu ....................... | B32B 27/28 442/340 |
| 2003/0054035 A1* | 3/2003 | Chu ..................... | C12N 5/0068 424/486 |
| 2003/0100944 A1* | 5/2003 | Laksin ................... | D04H 1/728 623/1.44 |
| 2004/0037813 A1* | 2/2004 | Simpson ................ | A61L 15/32 424/443 |
| 2005/0137675 A1* | 6/2005 | Dubson .................... | D01F 6/70 623/1.42 |
| 2006/0085063 A1 | 4/2006 | Shastri et al. | |
| 2006/0094320 A1* | 5/2006 | Chen ....................... | D04H 1/42 428/218 |
| 2006/0204539 A1* | 9/2006 | Atala ........................ | D01F 4/00 424/423 |
| 2006/0263417 A1* | 11/2006 | Lelkes .................... | C12M 25/14 424/443 |
| 2006/0264140 A1* | 11/2006 | Andrady .............. | D04H 1/4291 442/341 |
| 2007/0025972 A1* | 2/2007 | Rodriguez ........... | C12N 5/0667 435/366 |
| 2007/0152378 A1* | 7/2007 | Kim ........................ | D01F 6/70 264/465 |
| 2008/0065123 A1* | 3/2008 | Yli-Urpo ................ | C03C 25/26 606/151 |
| 2008/0112998 A1* | 5/2008 | Wang ..................... | A61K 35/33 424/423 |
| 2008/0208323 A1 | 8/2008 | El-Kurdi et al. | |
| 2008/0208325 A1 | 8/2008 | Helmus et al. | |
| 2008/0220054 A1* | 9/2008 | Shastri ..................... | A61P 25/20 424/443 |
| 2008/0254091 A1* | 10/2008 | Lee ......................... | D01D 5/003 428/221 |
| 2008/0292839 A1* | 11/2008 | Wei ............................ | A61F 2/02 428/113 |
| 2009/0018643 A1 | 1/2009 | Hashi et al. | |
| 2009/0030504 A1 | 1/2009 | Weber et al. | |
| 2009/0074832 A1* | 3/2009 | Zussman ............... | A61L 27/3821 606/151 |
| 2009/0196901 A1* | 8/2009 | Guilak .................... | A61P 19/02 435/6.16 |
| 2009/0248131 A1 | 10/2009 | Greenan | |
| 2010/0093093 A1* | 4/2010 | Leong ..................... | A61L 27/60 521/149 |
| 2010/0234955 A1 | 9/2010 | Santerre et al. | |
| 2011/0031656 A1* | 2/2011 | Anneaux .................. | F16L 11/12 977/788 |
| 2012/0058100 A1* | 3/2012 | Shastri .................... | A61K 47/34 424/94.4 |
| 2012/0059399 A1 | 3/2012 | Hoke et al. | |
| 2012/0171256 A1 | 7/2012 | Zhang et al. | |
| 2013/0183352 A1* | 7/2013 | Xie .......................... | A61L 27/54 623/23.72 |
| 2013/0197664 A1* | 8/2013 | Ballard .................. | B01D 39/04 623/23.72 |
| 2013/0268062 A1* | 10/2013 | Puckett ..................... | A61F 2/07 156/190 |
| 2014/0004159 A1* | 1/2014 | Xie .......................... | A61L 27/18 424/572 |
| 2014/0030315 A1* | 1/2014 | Johnson ............... | A61L 27/3804 424/444 |
| 2014/0081414 A1* | 3/2014 | Hall ....................... | A61L 31/048 264/413 |
| 2014/0141152 A1* | 5/2014 | Sostek ............... | D04H 1/43835 427/2.24 |
| 2014/0363484 A1* | 12/2014 | Koyakutty ........... | A61K 31/175 424/443 |
| 2015/0212071 A1* | 7/2015 | Berry .................... | C12N 5/0602 435/284.1 |
| 2015/0230918 A1 | 8/2015 | Detamore et al. | |
| 2015/0230953 A1 | 8/2015 | Bar et al. | |
| 2016/0250048 A1* | 9/2016 | Hall ......................... | A61F 2/945 623/1.44 |
| 2016/0361155 A1* | 12/2016 | Van Kampen ............ | A61F 2/08 |
| 2020/0015962 A1 | 1/2020 | Detamore et al. | |
| 2020/0149198 A1* | 5/2020 | Johnson .................. | A61L 27/38 |

OTHER PUBLICATIONS

Cheng et al. "Engineering the Microstruccture of Electrospun Fibrous Scaffolds by Microtopography" 2013, BioMacromolecules 14:1349-1360.

Liu et al. "Electrospun Fibrous Mats on Lithographically Micropatterned Collectors to Control Cellular Behaviors" 2012, Langmuir 28:17134-17142.

(56) References Cited

OTHER PUBLICATIONS

*Nanofiber Solutions, LLC* v. *Acera Surgical, Inc.*, IPR2021-01016, Petition (PTAB May 28, 2021).

* cited by examiner

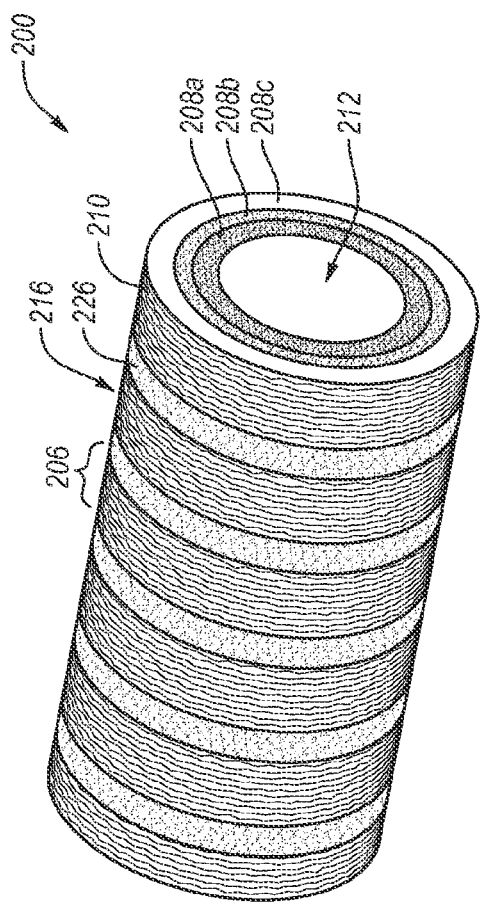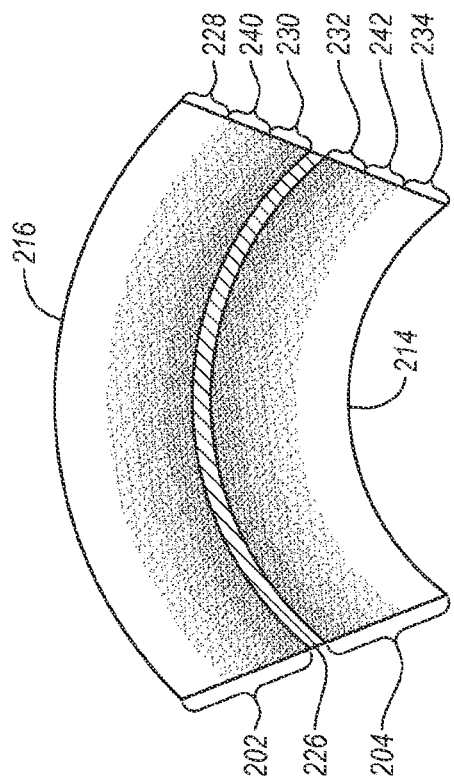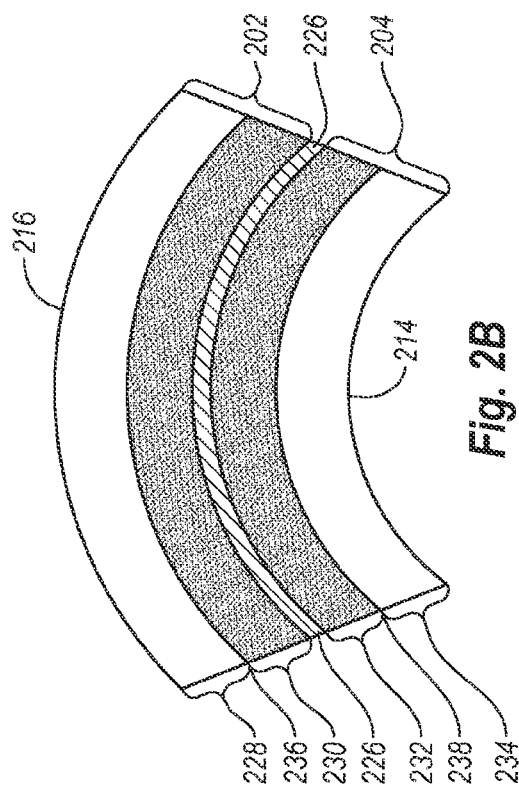

BIOMATERIAL BASED ON ALIGNED FIBERS, ARRANGED IN A GRADIENT INTERFACE, WITH MECHANICAL REINFORCEMENT FOR TRACHEAL REGENERATION AND REPAIR

CROSS-REFERENCE

This patent application is a continuation of U.S. patent application Ser. No. 16/570,510, filed Sep. 13, 2019, which is a continuation of U.S. patent application Ser. No. 14/239,049, filed Jan. 5, 2015, which is a U.S. national stage filing under 35 U.S.C. § 371 of International Application No. PCT/US2012/050974, filed Aug. 15, 2012, entitled "Fibrous Tracheal Patch," which claims the benefit of U.S. Provisional Application Ser. No. 61/523,894, filed on Aug. 16, 2011. The contents of each of these applications are hereby incorporated by reference in their entireties.

GOVERNMENT RIGHTS

This invention was made with government support under NSF 0847759 awarded by the National Science Foundation. The government has certain rights in the invention.

BACKGROUND

Tracheal repair procedures date back to the late 19th century. However, a predictably effective treatment is not available to restore normal function to a stenotic (e.g., abnormal narrowing) trachea without the use of an autologous tissue graft, which results in the sacrifice of native tissue. Even with the use of an autologous graft, the size, shape, and stiffness of the graft is often not ideal. Countless tissue engineering and regenerative medicine studies have attempted to regenerate tracheal tissue. Thus, there remains a need in the art for improvement in artificial tracheal implants

DESCRIPTION OF FIGURES

FIG. 2A includes a schematic representation of an embodiment of a fibrous implant having external structural reinforcing members.

FIG. 2B includes a schematic representation of an embodiment of a fibrous implant having sharp interfaces between different fiber types.

FIG. 2C includes a schematic representation of an embodiment of a fibrous implant having gradient interfaces between different fiber types.

DETAILED DESCRIPTION

Figure 1A:
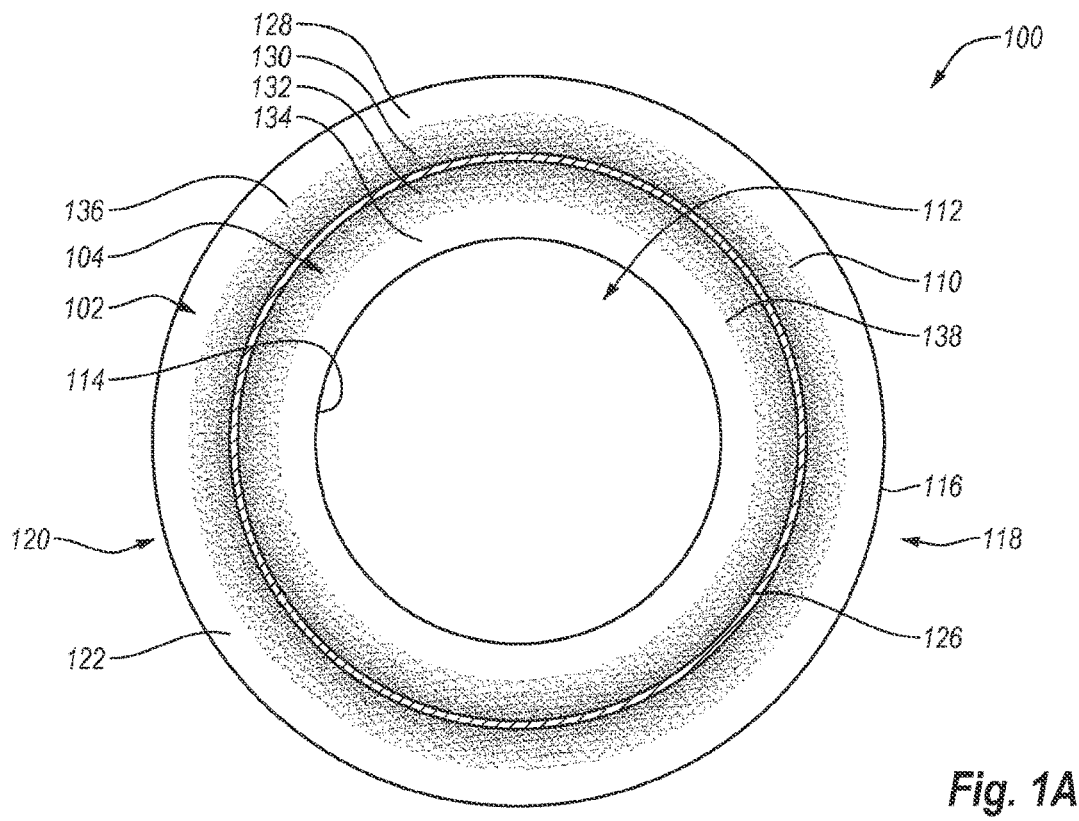
FIG. 1A includes a schematic representation of a cross-sectional profile of an embodiment of fibrous implant.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes fibrous biomaterial compositions that are prepared with or without mechanical reinforcement and that are suitable for use as implants. The implants can be configured for tissue regeneration and repair as well as for other uses. The implants can include biocompatible fibers arranged in a manner that facilitates implantation in order to promote biocompatibility as well as cell or extracellular matrix ingrowth into the implant between the fibers or to replace degraded fibers. The implant can have aligned fibers to random fibers, and can be configured for short or long term use, such as by being biostable or biodegradable. The overall implant or individual fibers can include or be devoid of polymeric coating compositions over a structural core or thread or ribbon. The individual fibers can be cylindrical polymers with regular or irregular cross-sectional profiles. The individual fibers can include active agents, such as antimicrobials or pharmaceuticals or tissue growth factors. The fibers and fibrous implant can be configured particularly for tracheal application, such as being arranged together for use as a tracheal implant. The fibrous implant may also be configured as other types of implants in other applications, such as esophageal, intestinal, arterial, or other body lumen or patch for a body lumen or tissue patch.

In one embodiment, the individual fibers can have a uniform composition. For example, the fiber can be prepared from a biocompatible material (e.g., biostable or biodegradable), such as a polymer, metal, ceramic, glass, bioglass (e.g., biodegradable) composite, alloy, or combination thereof.

In one embodiment, the individual fibers can be solid and uniform, or have a core and shell cross-sectional profile. When uniform, the fibers can have any of the properties described for a core and/or shell. The core can be a structural material that provides shape and structural properties to the fiber. The core can be flexibly resilient, deformable, or rigid. The core can be modified to have properties as desired so that the implant can range from being malleable or deformable or bendable to shape-set or rigid. The core can be a polymer, metal, ceramic, glass, composite, alloy, or combination thereof, which is harder or more rigid or more structurally sound compared to the shell. The core can also include bioactive agents as described herein. The shell can be a polymeric material that is commonly used for biomedical applications on implants. The polymeric shell can encapsulate the core. The polymeric shell can also include bioactive agents as described herein. The shell can be a polymer, metal, ceramic, glass, composite, alloy, or combination thereof, which is softer or less rigid or more structurally sound compared to the shell.

The individual fibers can be prepared from polymeric scaffold materials, such as materials that can be based on polymeric electrospun fibers (e.g. polycaprolactone, or poly (lactic-co-glycolic acid) that are fabricated to form an implant in a graded-manner (i.e., gradual transition between two polymeric layers) using a co-electrospinning technique. Other examples of polymers that can be used for the fibers and implant can include synthetic rubber, Bakelite, neoprene, nylon, PVC, polystyrene, polyethylene, polyetheylene oxide, poly(ethylene terephthalate), polylactate, polylactic acid, polyglyconate, polyglycolic acid, polypropylene, polyacrylonitrile, PVB, silicone, polydimethylsiloxane, polyurethane, and many more including blends or combinations of any of these polymers. The polymers can be biodegradable or biostable. The individual fibers or overall implant can include bioactive material components (e.g., bioactive glass strips), nanophase materials (e.g., chondroitin sulfate), or proteins (e.g., growth factors like transforming growth factor beta (TGF-beta) and epidermal growth factor (EGF)) as well as any well-known component of a composition for implantation.

The fibrous implant can be shaped into various forms (e.g., tubular, sheets, patches). The fibrous implant can include shapes that are solid through their core as well as hollow or luminal, where the cross sectional profiles can include triangles, squares, rectangles, rhombus, trapezoidal, and any other polygonal shape as well as circular or oval shapes or combinations of polygons with circular features.

The implant can be prepared from one type of fiber. Alternatively, the implant can be prepared from two or more types of fibers. The fibers can be arranged to have one type of fiber at one end or on one side, and then have a different type of fiber on the other end or other side. The implant can include one or more different types of fibers between the first end and other end. Any number of different types of fibers can be used. The different fibers can be arranged with a sharp interface therebetween with one type of fiber on one side of the sharp interface and a different type of fiber on the other side of the interface. Alternatively, the interface can be a gradient interface with corresponding gradients of the different types of fibers. In one aspect, the implant can have a first discrete portion with a first type of fiber and a second discrete portion adjacent to the first discrete portion with a sharp interface therebetween and where the second discrete portion has a second type of fiber. Optionally, the first discrete portion can be devoid of the second type of fiber, and/or the second discrete portion can be devoid of the first type of fiber. Alternatively, the first and second discrete portions can have gradients of both types of fiber. In one aspect, the implant can have two or more types of fibers where the fibers are arranged in a gradient from one end to the other. That is, a fiber of a first type can be on one side of the implant with a fiber of a second type being on the opposite side of the implant such that a gradient of the different types of fibers exists between the two ends. Various gradients from one end or one side to an opposite end or side can be prepared with different types of fibers. The gradient can be linear, curved, arcuate, or parabolic.

In one embodiment, the fibers can be arranged in a manner where fibers having a first characteristic are at a higher concentration or amount at one side or end of the implant and a lower concentration or amount at the other side or end of the implant so as to form a gradient. The fiber gradient can be constant, variable, parabolic, or the like. The fiber gradient may also be from one portion within the implant to another portion within the implant or to a side or end of the implant. For example, the fiber gradient can be from one side or end to an internal portion of the implant, such as a middle portion or center of the implant (e.g., at a support member). A fiber gradient may also be designed from one surface or end to a middle portion and then a different or same type of fiber gradient to the opposite side or end, which can be exemplified as a parabolic gradient. There may also be more than one fiber characteristic with a gradient distribution from one side or end to an opposite side or end. The fiber gradients can be from different types of fibers with different mechanical or chemical characteristics. The different characteristics can be the presence or absence of active agents in fibers to form one or more active agent gradients in the implant. Instead of having a hard or sharp interface between fiber groups with different characteristics, the different fibers can be arranged in a gradual or gradient interface between them so that the fibers with different characteristics are present in a gradient distribution. The materials of the different fibers may also be different, which can result in different degradation rates or active agent release rates from the fiber materials.

In one embodiment, the implant having the fibers can have a cross-sectional profile that includes the combined cross-sectional profiles of the individual fibers. That is, the fibers can be aligned so that the cross-sectional profile of the implant bisects the individual fibers. The individual fibers can be arranged or aligned as described herein. Also, the individual fibers can be arranged in the implant in the manner, gradients, or other patterns described in application Ser. No. 12/248,530 (hereinafter, the '530 application) for microspheres, which is incorporated herein by specific reference in its entirety. That is, the fibers can be arranged to provide the implant with a cross-sectional profile according to the implants of the '530, where the fibers replace the microparticles from one side to another side of the implant such as described in any of FIGS. 2A-2D, 4A, 6A-6D, 7A-7C, or combinations thereof. The fibers can be melded as described in the '530 application. Here, each fiber can extend from one end to another, where the fibers are arranged in the gradient from one side to an opposite side. The fibers may also be circumferentially aligned so that the same fiber encircles the implant one or a plurality of times.

The implant can be configured to be a functional tissue engineered scaffold that harnesses gradient scaffold design and drug delivery for tissue repair. One exemplary use described herein includes using the implant having the fibers for tracheal defect repair, where the fibers can be arranged circumferentially or in the direction of collagen fibers of the trachea. The implant can be pre-shaped or shaped in the operating room. The implant can be prepared in various sizes to accommodate patients from fetal to large adult sizes as well as for various sizes of defects or tracheal holes that may form or be formed in the trachea. The implant can be of a shape and dimension to be sufficient to be placed into and fill a void in tracheal tissue. For example, a surgeon can cut out the desired shape by a scalpel to provide a custom shape, or a cookie-cutter type cutting device can be pressed into the implant to provide a pre-determined shape. The surgeon can then suture or otherwise implant the shaped implant to the trachea in order to patch the tracheal defect. Alternatively, an adhesive, such as a wound glue adhesive, can be used to adhere the implant to the trachea.

In one embodiment, the implant can use biomaterials formed into a biocompatible scaffold that does not use any donor tissue. The implant can be manufactured at an industrial scale that provides a deliverable end product with a fiber gradient that provides a gradient of growth factors of a gradient of material composition. The implant can be structurally self-supportive by the fibers or it can be prepared to have some structural component that reinforces the scaffold to provide the appropriate mechanical integrity to keep the airway from closing. The individual fibers can include a structural reinforcement member, such as a core, shell, edge, or linear filament member. The individual fibers may also be electrospun into an implant around or encapsulating a structurally reinforcing member that is retained within the implant. For example, a tube member of a certain material can be used for structure, and the fibers can be electrospun around the tube member, such as on the luminal wall and outer wall of the tube so that the entire tube member is encapsulated by electrospun fibers.

Preliminary studies have shown that rabbits survived and grew new tissue over polycaprolactone (PCL) electrospun scaffolds that were used to patch a trachea defect. Another implant may include a faster degrading alternative to PCL. Also, gradients of fast and slow degrading materials can be from side to side or from a side to the middle of the implant. The electrospun fiber gradient can be configured to allow greater tissue in-growth, while not compromising the mechanical stability of the construct. This is achieved by incorporating faster degrading polymers like poly(lactic-co-glycolic acid) (PLGA) into the PCL using a coelectrospinning process (e.g., using two or more syringes and power supplies) to create multicomponent fibrous scaffolds.

Some exemplary novel and beneficial features of embodiments of the fibrous implant include: the scaffolding material includes aligned fibers (e.g., aligned electrospun fibers); the microenvironment of the fibrous scaffold mimics native extracellular matrix (ECM) and supports cell attachment, differentiation, and growth; and circumferentially aligned fibers mimic the collagen in native tracheal cartilage, where the outer superficial zones of cartilage have circumferentially aligned collagen fibers (which are active in tensile resistance). As such, the implant can be configured to function as a native tracheal segment with the fibers aligned similar to the collagen fibers of the trachea. The fibers of the implant may also include collagen coatings for enhanced biocompatibility. Collagen fibers may also be used. Also, the method of manufacturing can include electrospinning the fibers, which can be adapted to provide for a tracheal implant having circumferentially aligned fibers, or aligned in any manner.

While the present invention has been described as being manufactured by electrospun fibers, other manufacturing methods can be employed. For example, the individual fibers can be extruded and bound at their ends to form an implant. Also, individual fibers can be aligned and then coupled together at their ends and/or one or more discrete locations along the aligned fibers. Extruded or molded fibers may also be encapsulated in a polymeric coating. Other manufacturing techniques may also be suitable for forming the fibrous.

In one embodiment, the fibrous implant can include a plurality of fibers in a multilayer, gradient design that simulates the epithelium and cartilage layers in the trachea. That is, the implant can include fibers aligned to simulate the epithelium and fibers aligned to simulate the cartilage with a suitable interface or gradient therebetween. In each layer or in each fiber of each layer, specific polymers and bioactive components can be tailored to meet the specific regeneration requirements of the tissue. For example, PLGA can be used in the outer electrospun layers as the faster degrading layer to allow for cells to colonize the scaffold; while PCL, a slower degrading polymer, can be used in inner layers of the scaffold to maintain structural integrity. Fibers or support members having biodegradable glass or other biocompatible material can be at a middle or center portion of the implant.

In one embodiment, the fibrous implant can include a structural reinforcing member along with the fibers to provide for further mechanical stability in the scaffold. For example, the implant can include one or more bioactive glass strips that are sufficient to withstand the tracheal compressive and tensile forces and prevent against tracheal collapse. The bioactive glass strips can be arranged circumferentially, longitudinally, diagonally, helically, and/or be distributed evenly or randomly through the scaffold. The bioactive glass strips can be distributed and arranged so as to mimic the native cartilage rings. Also, the bioactive glass can be tubular or annularly arranged with a circumference that matches the trachea.

The implant can be used in cell culture to grow suitable cells prior to implantation. The implant having cells or cell cultures attached thereto can then be implanted into a subject. Accordingly, the implant can be used with or without cells, and does not require specialized surgical techniques or highly invasive, multistage surgeries. This straightforward, highly adaptable, patient-specific approach for a tracheal implant can benefit medical practitioners and patients.

While the present implant having fibers (e.g., in a gradient configuration) has been described for use in tracheal defect repair, the implant may also be dimensioned, shaped, or otherwise configured for implantation in other tissue engineering applications (e.g., vascular tissue engineering), or possibly even wound or tissue regeneration (e.g., skin, liver, etc.). Thus, the technology of the fibrous implant is not limited in its focus, and can be configured for any implant application. The fibrous implant can be configured for use in patch tracheal defects and whole circumferential defects, and thereby can be used as any patch or for any body lumen. For example, non-reinforced implants may be used for tracheal patches while reinforced implants can be used for circumferential implants. The device can be enhanced in mechanical performance by incorporating resilient materials such as bioactive glass strips, sheets, or tubes, which serve to keep the biomaterial structurally stable (i.e., prevent collapse).

In one embodiment, computer modeling can be used to design an implant having a gradient in one or more characteristics. The computer model can receive experimental or theoretical data and design an implant that is suitable for the intended use. The computer model can determine the best way to assemble the gradient of fibers and when and where to include one or more bioactive or structural materials in the fibers. The computer can then control the electrospinning in order to prepare the fibrous implant. The computer can be programafig.med to prepare the implant with certain characteristics. Also, the computer can receive data of a subject in need of an implant, and then determine the structure and fibers and fiber gradients or sharp interfaces for the implant to match a defect to be treated with the implant.

The fibrous implant can be provided in a generic shape, and then a medical professional can pre-shape the implant before an operation, or easily create custom shapes during surgery. Pre-shaped fibrous implants can also be tailored and customized before implantation. The generic shape can be a tube similar in size and configuration to a trachea. The fibers of the implant can extend from one end of the tube to the other end of the tube or be circumferentially aligned or wound. The fibers can be wound circumferentially similar to thread wound on a spool. The body of the fibers can cooperatively form the luminal surface and outer surface of the tubular generic shape. The implant can be sutured in place and/or placed with a bioadhesive, or any other method of implantation and securement commonly used for implants can be used.

Figure 1B:
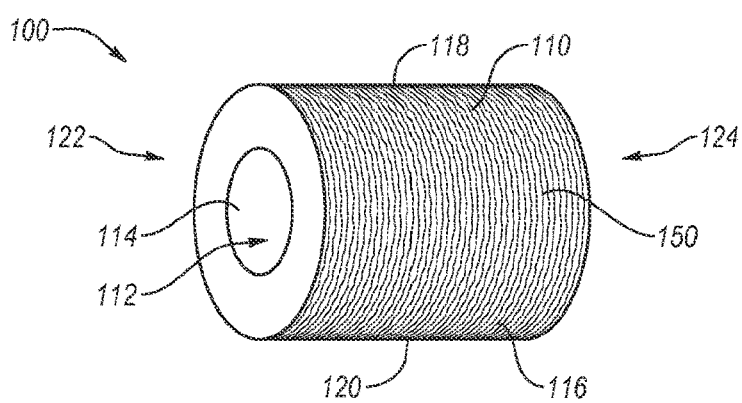
FIG. 1B includes a schematic representation of the fibrous implant of FIG. 1A.

FIGS. 1A-1B illustrate an embodiment of a fibrous implant 100 in accordance with the principles described herein. The fibrous implant 100 is shown to have a tubular body 110 with a lumen 112. The tubular body 110 extends from a luminal wall 114 to an outer wall 116. The tubular body 110 can also be considered to have one side 118 and an opposite side 120. The tubular body 110 has a first end 122 and an opposite second end 124. As shown in FIG. 1A, the tubular body 110 is pointing out from the page with the first end 122 being viewable. The individual fibers 150 can be wound circumferentially from the first end 122 to the second end 124 and back, depending on the layer, as shown in FIG. 1B. FIG. 1A shows the fibers 150 to be arranged around a support member 126. However, the support member 126 can be optional. The tubular body 110 is shown to have a first annular section 102 extending from the outer wall 116 to the support member 126 and a second section 104 extending from the support member 126 to the luminal wall 114.

The first section 102 can be prepared from one or more different types of fibers. For example, the first section 102 can have a first type of fiber 128 adjacent to the outer wall 116 and a second type of fiber 130 adjacent to the support member 126. The interface 136 between the first type of fiber 128 and second type of fiber 130 can be a hard interface or a gradient interface. In the gradient interface 136, the first type of fibers 128 can fade into the second type of fibers 130, and vice versa. As such, the outer wall 116 can be mostly or all the first type of fibers 128 and adjacent to the support member 126 can be mostly or all second type of fibers 130. Also, the second section 104 can be prepared from one or more different types of fibers. For example, the second section 104 can have a third type of fiber 132 adjacent to the support member 126 and a fourth type of fiber 134 adjacent to the luminal wall 114. The interface 138 between the third type of fiber 132 and fourth type of fiber 134 can be a hard interface or a gradient interface. In the gradient interface 138, the third type of fibers 132 can fade into the second type of fibers 134, and vice versa. As such, the luminal wall 114 can be mostly or all the fourth type of fibers 134 and adjacent to the support member 126 can be mostly or all third type of fibers 132.

In one aspect, the first type of fiber 128 and fourth type of fiber 134 can be the same; however, they can be different. In one aspect, the second type of fiber 130 and third type of fiber 132 can be the same; however, they can be different. In one aspect, the first type of fiber 128 and third type of fiber 132 can be the same; however, they can be different. In one aspect, the second type of fiber 130 and fourth type of fiber 134 can be the same; however, they can be different. Other permutations of fiber distributions can also be used.

The support member 126 can be an annular member, tubular member, or it can be a "C" shape or other suitable shape, such as a helix, spiral, or the like. The support member 126 can be a single piece or multiple pieces, as shown in FIG. 2A below. The support member 126 can be on the luminal wall 114 or outer wall 116 instead of being embedded within the fibers 150. The support member 126 can be a plurality of rigid fibers aligned with the other fibers 150. The support member 126 can be omitted, such as when one or more of the fibers 150 or fiber types are sufficient for structural integrity for use as an implant. Such structural integrity can be sufficient for being used as a tracheal implant.

While the fibrous implant 100 is shown to be tubular, any other shape can be used. The fibrous implant 100 can be solid or hollow. The fibrous implant 100 can have a cross-sectional profile that is circular, triangle, square, rectangular, or other polygon shape that is hollow with a lumen or solid without a lumen. In one embodiment, the fibrous body can have the shape of a tube, sheet, "C", diamond, rounded diamond, polygon, circular, or oval shape or irregular shape. In one aspect, the fibrous body can have an irregular shape designed to conform to a correspondingly shaped tracheal defect. The fibrous body can have a predefined shape. In one aspect, the fibrous body is sized for a fetus or infant or child to adolescent or teen or young adult or small adult or average male or female adult or large adult or an animal. Fibrous composition can be prepared as any type of implant in any shape that is suitable to be prepared from fibers. A coating can be applied to the outside of the implant to contain the fibers therein. Also, the fibers can be adhered together. Additionally, the fibers can be melded together with a solvent. In any event, the fibers can be bound together to form a three-dimensional implant. The fiber gradient can be with respect to the inner wall 114 and/or outer wall 116 or support member 126. The fiber gradient can be with respect to the first side 118 or second side 120. The fiber gradient can be with respect to the first end 122 or second end 124.

In FIGS. 1A-1B, one of the polymers can be PLGA while the other is PCL. For example, the fibers adjacent to the lumen or outside can be PLGA while the fibers adjacent to the support member can be PCL. The support member can be a bioactive glass ribbon.

Figure 1C:
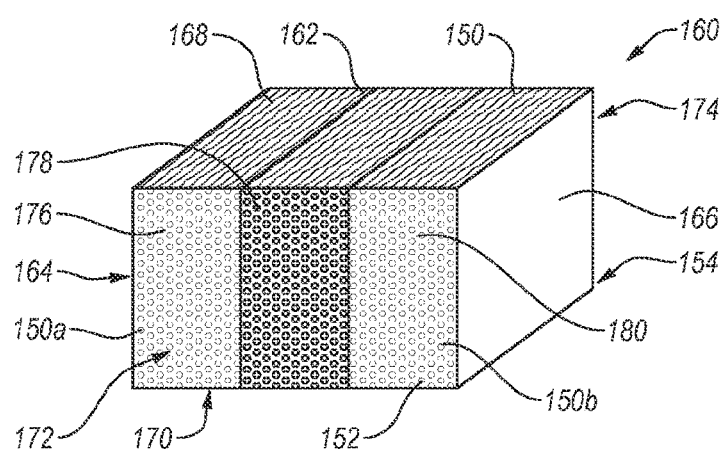
FIG. 1C includes a schematic representation of an embodiment of a fibrous implant.

FIG. 1C shows a fibrous implant 160 in the form of a solid three-dimensional block 162. The block 162 can have a first side 164 and an opposite second side 166, and have a top side 168 and opposite bottom side 170. The fibers 150 can extend from a first end 172 to opposite second end 174. The fibers 150 can have first fiber ends 152 and opposite second fiber ends 154. The block 162 can have the fibers 150 arranged with a first type of fiber 150a at the first side 164, where the first type of fibers 150a form a first portion 176. The block 162 can have the fibers 150 arranged with a second type of fiber 150b at the second side 166, where the second type of fibers 150b form a second portion 180. A third portion 178 is positioned between the first portion 176 and second portion 180. The third portion 178 can include a third type of fiber or it can be a gradient distribution of the first type of fiber 150a and second type of fiber 150b. For example, in the third portion 178, the first type of fiber 150a can have a higher concentration adjacent to the first portion 176 and lower concentration adjacent to the second portion 180, and the second type of fiber 150b can have a higher concentration adjacent to the second portion 180 and lower concentration adjacent to the first portion 176.

FIG. 2A illustrates another embodiment of a fibrous implant 200 with a tubular body 210 with a lumen 212, which has a support member 226 on the outer wall 216. While five different support members 226 are shown, any number can be used, and positioned at any location with gaps 206 or adjacent or touching. The tubular body 210 can include a first section 208a, second section, 208b, and third section 208c, each section having a different type of fiber, or the second section 208b can be a blend of the fibers of the first section 208a and the third section 208c. The support member 226 can be an annular member, or it can be a "C" shape or other suitable shape, such as a spiral, or the like. The support member 226 can be bioactive glass ribbons, which can have a rectangular cross section, be long and straight, and be capable of springing back to being straight if bent and released. The support member 226 can be about 800 μm wide (e.g., or +/1 5%, 10%, or 20%), 100 μm thick (e.g., or +/1 5%, 10%, or 20%), and vary in length (e.g., 8-10 cm) (e.g., or +/1 5%, 10%, or 20%). To mimic the rabbit trachea, where cartilage rings are very narrow (~1 mm) and closely spaced (~1 mm in between), the support member 226 ribbons can be spaced 1 mm apart from each other along the length. The ribbons can be wrapped around the construct and secured with liquid PCL solution (see FIG. 3).

FIG. 2B shows a portion of an embodiment of the fibrous implant 200 that can be used. The fibrous implant 200 is shown to have an inner wall 214 and outer wall 216. The fibrous implant 200 is shown to have a first section 202 extending from the outer wall 216 to the support member 226 and a second section 204 extending from the support member 226 to the inner wall 214. The first section 202 can have a first type of fiber 228 adjacent to the outer wall 216 and a second type of fiber 230 adjacent to the support member 226. The interface 236 between the first type of fiber 228 and second type of fiber 230 is a sharp interface, such that there is substantially none of the first type of fiber 228 mixed with the second type of fiber 230. Also, the second section 204 can have a third type of fiber 232 adjacent to the support member 226 and a fourth type of fiber 234 adjacent to the inner wall 214. The interface 238 between the third type of fiber 232 and fourth type of fiber 234 is a sharp interface, such that there is substantially none of the third type of fiber 232 mixed with the fourth type of fiber 234.

FIG. 2C shows a portion of another embodiment of the fibrous implant 200 that can be used. The fibrous implant 200 is shown to have an inner wall 214 and outer wall 216. The fibrous implant 200 is shown to have a first section 202 extending from the outer wall 216 to the support member 226 and a second section 204 extending from the support member 226 to the inner wall 214. The first section 202 can have a first type of fiber 228 adjacent to the outer wall 216 and a second type of fiber 230 adjacent to the support member 226. A gradient interface 240 is located between the first type of fiber 228 and second type of fiber 230 such that there is first type of fiber 228 mixed with the second type of fiber 230 in gradients. Also, the second section 204 can have a third type of fiber 232 adjacent to the support member 226 and a fourth type of fiber 234 adjacent to the inner wall 214. A gradient interface 242 is located between the third type of fiber 232 and fourth type of fiber 234 such that there is third type of fiber 232 mixed with the fourth type of fiber 234 in gradients. The gradients can be linear or curved as shown in the '530 Application.

The fibrous body can include one or more different types of fibers, such as at least two different types of fibers, or a plurality of different types of fibers that are aligned in the same direction. The fibrous body can have a first type of fiber having a first characteristic in a first gradient distribution across at least a portion of the fibrous body. A second type of fiber can have a second characteristic in a second gradient, which second gradient can be opposite of the first gradient. The different characteristics an include type of composition; type of polymer; fiber diameter size; fiber diameter size distribution; type of bioactive agent in a fiber; type of bioactive agent combination in a fiber; bioactive agent concentration in a fiber; amount of bioactive agent in a fiber, rate of bioactive agent release from a fiber; mechanical strength of a fiber; flexibility of a fiber; rigidity of a fiber; color of a fiber; radiotranslucency of a fiber; or radiopaqueness of a fiber. Some preferred examples of different characteristics can be different fibers having different: bioactive agents; antimicrobial agents; pharmaceuticals; structural reinforcing members; polymer type; fiber type; cell types attached to the fibers; fiber compositions thereof, and combinations thereof. In one aspect, the fibrous body can include different fibers with two or more characteristics in two or more gradient distributions or varying gradient distributions. In one aspect, the fibrous body can have a higher concentration of fibers having one or more characteristics on one side or end of the body than in the center and/or on an opposite side or end of the body. In one aspect, the fibrous body can have a higher concentration of fibers with one or more active agents on one side or end of the body than in the center and/or on an opposite side or end of the body. In one aspect, the fibrous body can have a higher concentration of fibers with structural reinforcing members, structural reinforcing fibers, or structural reinforcing members on one side or end of the body than in the center and/or on an opposite side or end of the body, or the reinforcing members can be centered or between the sides or ends of the body. In one aspect, the fibrous body can have PCL fibers in one gradient distribution and PLGA in another distribution.

In one embodiment, the implant can include a plurality of fibers forming an implant body having: a first set of fibers having a first gradient spatial distribution with a higher concentration at the first end and lower concentration at the second end of the body; and a second set of fibers that are different from the first set of fibers, the second set of fibers having a second gradient spatial distribution with a lower concentration at the first end and higher concentration at the second end of the body. In one aspect, the first gradient spatial distribution and second gradient spatial distribution blend into each other. In one aspect, the fibrous implant can include: a first portion at the first end having a majority of fibers of the first set; and a second portion at the second end having a majority of fibers of the second set. In one aspect, the fibrous implant can include: a first portion at the first end having a majority of fibers of the first set; a second portion at the second having a majority of fibers of the second set; and a third portion disposed between the first portion and the second portion, wherein the first gradient spatial distribution in the third portion forms a first concentration gradient of the first set of fibers and the second gradient spatial distribution in the third portion forms a second concentration gradient of the second set of fibers. In one aspect, the fibrous implant can include a first bioactive agent contained in or disposed on the first set of fibers, and the second set of fibers being substantially devoid of the first bioactive agent. In one aspect, the fibrous implant can include a first bioactive agent contained in or disposed on the first set of fibers, and a second different bioactive agent contained in or disposed on the second set of fibers. In one aspect, the plurality of fibers include polymeric fibers or having polymeric coatings that electrospun or melded together. In one aspect, at least one of the first set or second set of fibers is comprised of a biodegradable polymer, such PLGA. In one aspect, the fibrous implant can include live cells and a medium sufficient for growing the cells disposed in the interstitial spaces between the fibers. In one aspect, a first bioactive agent is contained in or disposed on the fibers of the first set, and a second different bioactive agent is contained in or disposed on the fibers of the second set. For example, the first bioactive agent can be an osteogenic factor and the second bioactive agent can be a chondrogenic factor. In another aspect, the different fibers can have a transforming growth factor (TGF)-$\beta_3$ and/or of epidermal growth factor (EGF) or keratinocyte growth factor (KGF) or vascular endothelial growth factor (VEGF). In one aspect, the first set of fibers have a first characteristic and are devoid of a second different characteristic, and the second set of fibers having the second different characteristic and are devoid of the first characteristic.

In one embodiment, the fibrous implant can include a plurality of live cells attached to the plurality of fibers. The cells can be any type of animal cell, such as human cells, or even cells of the subject to receive the fibrous implant. The fibrous implant can include a first cell type associated with a first set of fibers, and a different second cell type associated with a second set of fibers.

In one embodiment, a method of preparing tissue engineering scaffold for growing cells can be performed with the fibrous implant. The method can include: providing a first set of fibers; providing a second set of fibers different from the first set of fibers; and combining (e.g., electrospinning) the fibers of the first set and second set together so as to form a body. However, the fibers can be prepared during the electrospinning process, where a first composition is prepared into the first set of fibers and a second composition is prepared into the second fibers. Some of the fibers can be prepared so as to degrade over time. Also, some of the fibers can be prepared so as to release the bioactive agents to promote healing or tissue ingrowth into the fibrous implant. Multi layered and gradient scaffolds can be fabricated using a co-electrospinning process with two or more syringes in programmable syringe pumps.

In one embodiment, the fibrous body can have individual fibers with a first characteristic, wherein the fibers are arranged in a first gradient distribution across at least a portion of the fibrous body. In one aspect, the fibrous body can have different types of fibers having different characteristics with a fiber with one characteristic having a first gradient distribution with respect to one side or end of the implant and a different fiber having a second characteristic having a second gradient distribution with respect to a second side or end of the implant. In one aspect, the fibrous body can have different fibers having different characteristics with a fiber with one characteristic having a first gradient distribution with respect to a center point or plane of the implant and a fiber with a second characteristic having a second gradient distribution with respect to a side or end of the implant. Accordingly, the fibrous body can have a plurality of fiber layers from one side or end to another side or end. Each fiber layer can have a different type of fiber.

In one embodiment, the fibrous body can be formed so as to have fibers wound (e.g., substantially circumferentially) around a spool to form a wound fibrous body. The spool can be removed to form a tubular implant. The fibrous body can have fibers of a first type at one or more inner layers of the wound fibrous body and fibers of a second type at one or more layers of the wound fibrous body adjacent to the one or more inner layers. In one aspect, the fibers can be longitudinally aligned. Alternatively, the fibers can be laterally aligned. The fibers can be diagonally or helically aligned. In one aspect, the fibrous body can be formed so as to have fibers wound around a spool to form a wound fibrous body, with the fibrous body having: fibers of a first type at one or more inner layers of the wound fibrous body; fibers of a second type intermingled with the one or more inner layers of the fibers of the first type; and fibers of the second type at one or more second layers of the wound fibrous body adjacent to the one or more inner layers. In one aspect, the fibrous body can be formed so as to have fibers wound around a spool to form a wound fibrous body, with the fibrous body having: fibers of a first type at one or more inner layers of the wound fibrous body; fibers of a second type intermingled with the one or more inner layers of the fibers of the first type; fibers of the second type at one or more second layers of the wound fibrous body adjacent to the one or more inner layers; fibers of a third type or the first type intermingled with one or more second layers of the fibers of the second type; and fibers of the third type at one or more third layers of the wound fibrous body adjacent to the one or more second layers.

In one embodiment, the fibrous body can have the fibers aligned from top to bottom (e.g., superoinferiorly) with respect to implantation orientation of an upright subject. In one aspect, the fibrous body can have the fibers aligned from side to side (i.e., mediolaterally at the anterior aspect of the trachea; in the transverse plane) with respect to implantation orientation of an upright subject.

In one embodiment, the fibrous body can have void space sufficient for culturing cells within the implant or on one or more fibers. This can be from selective degradation of the fibers, laser etching after formation of the fibrous body, forming pores with solvent, or by the interstitial spaces between adjacent fibers. Also, the void space can form over time after implantation. The void space can include a cell culture media in in vitro application. The void space can include cells in in vitro or in vivo applications.

In one embodiment, the fibrous body can have one or more elongate structural members arranged at from about 0 degrees to about 90 degrees with respect to the aligned fibers, such as at about 10, 20, 30, 40, 45, 50, 60, 70, about 80 degrees. The angle can be made with respect to a longitudinal axis of the fibrous implant, a plurality of the fibers, direction of aligned fibers, or with respect to a single fiber. The direction of orientation can be the longitudinal axis of the trachea or circumferentially, and the structural members can be angled therewith.

In one example, the fibers can be aligned and arranged so as to mimic collagen arrangement in native tracheal cartilage. However, the fibers can also be random, unaligned, diagonally aligned, crisscrossed, helical, orthogonal, spun, woven, or other pattern. In one aspect, one or more of all of the fibers can be circumferentially aligned. In one aspect, the fibrous body can include different types of aligned fibers arranged so as to mimic collagen arrangement in native tracheal cartilage, where outer superficial zones of the implant mimic cartilage and has circumferentially aligned fibers that mimic collagen fibers. In one aspect, the fibrous body can include different types of aligned fibers arranged in multiple layers so as to mimic and/or promote regeneration of epithelium and cartilage layers in the trachea. In one aspect, one or more of all of the fibers are not aligned. In one aspect, one or more of the fibers can run circumferentially or laterally or longitudinally with respect to an upright position of a subject In one embodiment, the fibrous body can include fibers that are active in tensile resistance. As such, a force can be applied to opposite ends of the fibers. The fibers can be longitudinally stretched. As a baseline comparison, mechanical studies of the trachea have provided tensile moduli ranging from 0.3 to 14 MPa, and circumferentially aligned electrospun PCL and PLGA fibers have ranged from 10-45 MPa. The values can be modified when bioglass is used as a support member.

In one embodiment, the implant can include one or more fibers that has a core and shell cross-sectional profile. In one aspect, one or more fibers can have a core and multiple shells cross-sectional profile. The fibers can also be solid or a single material. The fibers can be tubular and hollow with an internal lumen. The fibers can have a cross-sectional profile dimension ranging from about 1 mm to about 50 mm in diameter, from about 2 mm to about 25 mm, from about 5 mm to about 20 mm, from about 8 mm to about 15 mm, or about 12 mm in diameter.

While a fibrous implant is described herein, it should be recognized that the implant can be a pre-implant or a generic shape that can be modified prior to implantation. That is, a scaffold, such as a tissue engineering scaffold for in vivo or in vitro applications, having the fibers arranged as described herein that is not implanted or prior to implantation can be considered to be a fibrous implant, and the features of the fibrous implant apply to pre-implant scaffolds as well as tissue engineering scaffolds.

In one embodiment, the fibrous implant having the features or characteristics described herein can be manufactured. A method of manufacturing a fibrous implant can include electrospinning fibers so as to form the electrospun fibrous body. The fibers can be electrospun to have a first characteristic in a first gradient distribution. The fibers can be electrospun to have a second characteristic in a second gradient different from the first characteristic and/or first gradient. In one aspect, the method of manufacture can include preparing the materials or compositions for the electrospun fibers and/or formation of the fibers therefrom. The method can include electrospinning an inner layer of fibers, and electrospinning one or more layers over the inner layer.

In one embodiment, the method of manufacture can include electrospinning the fibers around one or more structural reinforcing members (e.g., support member). The method can include placing circumferential structural reinforcing members around an electrospun layer, and electrospinning a layer of fibers over the reinforcing members. The method can include electrospinning one or more layers of aligned fibers around one or more circumferentially or longitudinally aligned elongate structural reinforcing members. Also, both the fibers and structural reinforcing members can be circumferentially orientated or longitudinally oriented. The structural reinforcing member can be bioactive glass. The cross-sectional dimensions of the bioactive glass reinforcing member can range from about 2 mm to about 25 mm in diameter, from about 5 mm to about 20 mm, from about 8 mm to about 15 mm, or about 12 mm. In one aspect, the implant can be configured with sufficient structural reinforcement members for functionality without collapsing or restenosis. In one aspect, the structural reinforcing members can hold the implant in shape and provide for resiliency for the implant to spring back to shape if deformed.

Figure 5:
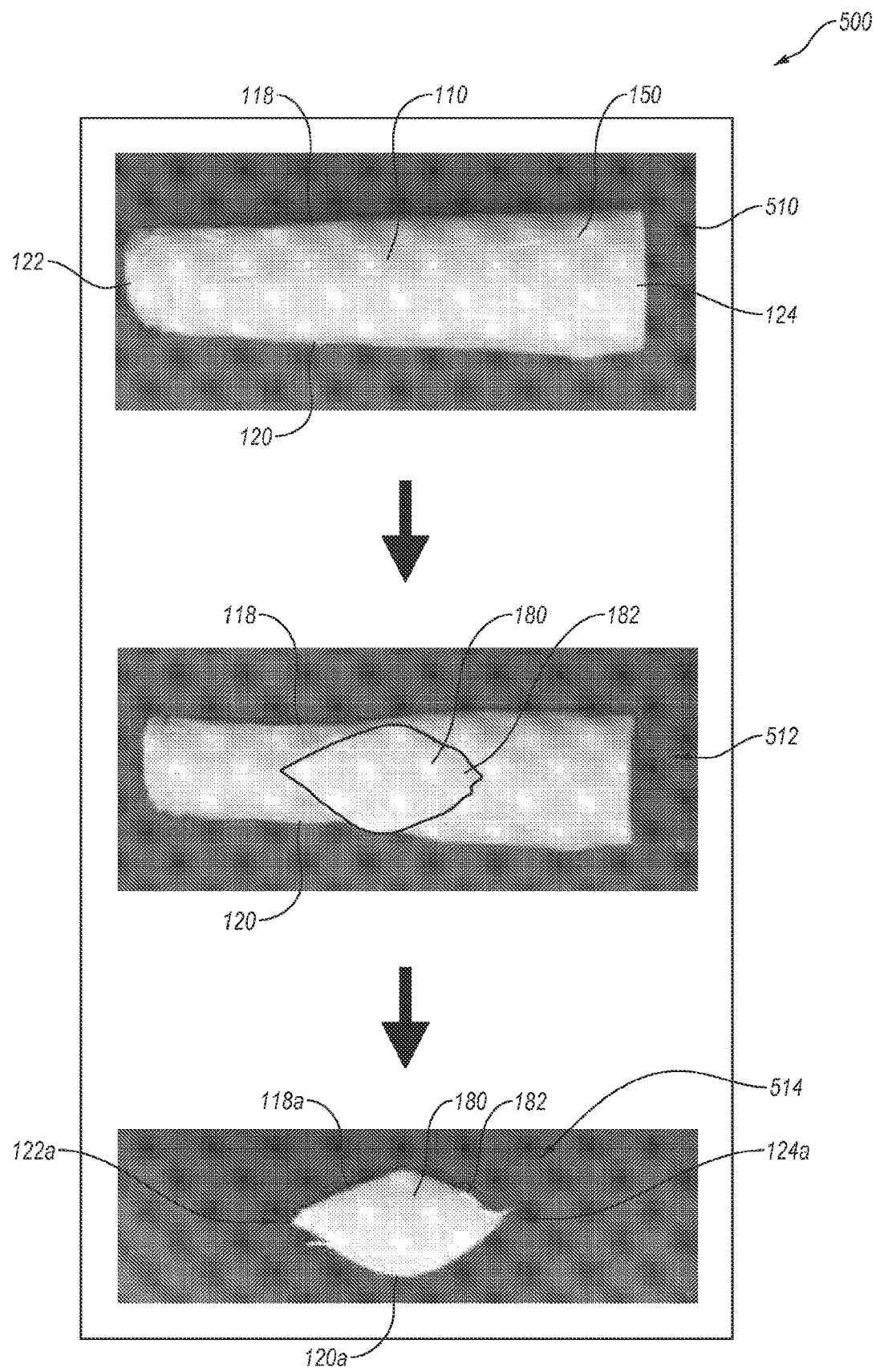
FIG. 5 illustrates a method of forming a fibrous implant patch from a tubular fibrous implant.

FIG. 5 illustrates a method 500 of manufacturing an implant. The top panel shows a tubular implant 510, which can be cut 512 into a patch 514. The tubular implant 510 can be the same as the implant 100 of FIGS. 1A-1B. The tubular implant 510 is cut along line 182 to form the body 180 of the patch 514. Here, the patch 514 is shown to have one side 118a and an opposite side 120a, and a first end 122a and an opposite second end 124a. The first end 122a or second end 124 can be the top or bottom of the patch 514 when implanted.

In one embodiment, the method of manufacture can include sterilizing the implant. Any method of sterilization can be used. For example, alcohol or other solvent can be used for sterilization. In another example, the implant can be subjected to heat and/or pressure for sterilization.

In one aspect, the fibrous body can be analyzed after manufacture. This can include analysis of the alignment pattern (e.g., circumferential alignment or non-alignment) of the fibers. The analysis can be performed as known in the art or described herein.

The fibrous implants can be configured for use as implants in any location within the body. However, the fibrous can be especially suitable for patch or circumferential implants for body lumens, such as the trachea, esophagus, intestine, or the like. While tracheal embodiments as described, the use can be applied to other body lumens.

In one embodiment, the fibrous implant can be used in a method of treating a tracheal defect. Such as method can include providing a tracheal implant as described herein, and implanting the tracheal implant into a tracheal defect in a subject. The subject can be a human or other animal. The implant can be shaped for a tracheal defect, and implanted into a defect in the trachea. The defect can be a circumferential defect, and the implant can be implanted in the circumferential tracheal defect. In one aspect, the defect can be a hole, and the implant can be used for patching the hole defect, such as for treating tracheal stenosis. The defect can be natural, an injury, or surgically prepared. The implant can be used for tracheal tissue regeneration.

In one aspect, a medical professional can custom shape the tracheal implant to match the defect. This can include providing an implant of any shape having fibers with any degree of alignment or random alignment to a medical professional where the medical professional shapes the implant prior to implantation.

Figure 3:
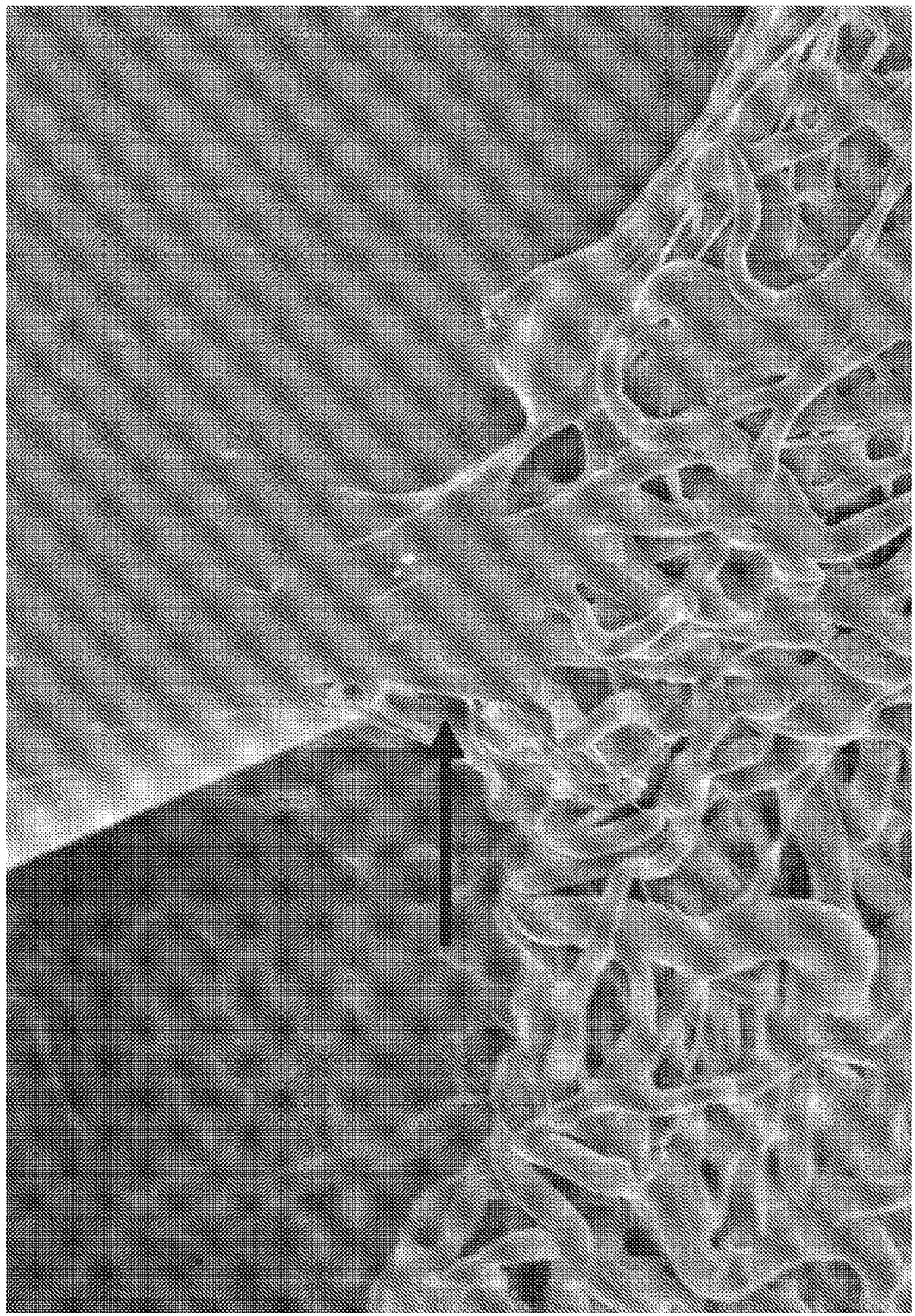
FIG. 3 includes an image of fibers associated with a structural reinforcing member.

The interface between the fibers and the support member can vary. In one instance, the fibers can be bonded to the support member, such as with melting, melding, adhesive or the like. In another instance, the fibers can encapsulate the support member. When the support member is bioglass, the fibers can be spun around the bioglass for encapsulation. Also, liquid polymer, such as the same or different polymer from the fibers, can be applied to the bioglass and fibers to promote association by the liquid polymer solidifying. FIG. 3 illustrates an example of an interface between the fibers and bioglass, where the arrow shows association of the fibers with the bioglass. FIG. 3 is an SEM image of bioglass ribbon (bulk object) encased in PCL fibers (thin spaghetti-like fibers). Liquid PCL was used to secured bioglass to fibers at contact points (see arrow). As such, the bioglass strips can be encapsulated within the fibrous sheets. The bioglass can also be encapsulated with PLGA or other polymers.

In one embodiment, one or more fibers can have chondroitin sulfate, while other fibers may or may not have chondroitin sulfate. The application of chondroitin sulfate in electrospun scaffolds can be useful.

In one embodiment, the fibers can be electrospun so as to be circumferentially oriented to mimic the tracheal structure. The circumferentially-oriented polymer fibers can be cut, placed, and sutured into a defect. Rings of bioactive glass can be used to reinforce the electrospun fiber scaffold to provide the mechanical integrity. The implant can have a circumferential fiber structure of the native trachea collagen from the electrospun fibers in the circumferential orientation as well as the rings of the native trachea mimicked by the bioactive glass ribbons also in the circumferential orientation. The fibers can be spun to form gradients in order to accelerate regeneration as the different fibers of the different gradients can have different characteristics. For example, one fiber can be configured for regenerating cartilage-like tissue and another for regenerating ciliated epithelium, where the different fibers fade as gradients into each other from one side of the implant to the other. When the implant is cylindrical or cut from a cylindrical member, the fibers can have axial gradients from an outer surface to luminal wall, and vice versa. The gradients can also extend from a wall to an internal support member. The fiber gradients can provide gradient concentrations of transforming growth factor (TGF)-$\beta_3$ (e.g., outer wall layers) for chondrogenesis and epidermal growth factor (EGF) (e.g., inner or luminal wall layers) for epithelialization. The implant can be properly implanted with these orientations of these types of fibers. In one aspect, the fibrous implant can be seeded and/or cultured with bone marrow derived mesenchymal stem cells (BMSCs) and/or umbilical cord mesenchymal stromal cells (UCMSCs) or different gradients thereof. The gradient distribution of the fibers with different growth factors provides a release gradient so that the different growth factors are released and present in the subject in the gradient distribution. The fibers can be loaded with various amounts of TGF-$\beta_3$ and/or EGF (e.g., 0, 1, or 10 ng of growth factor per 1 mg of polymer, such as PLGA). However, the fibrous implant can be with or without growth factors or with or without cells.

Figure 4B:
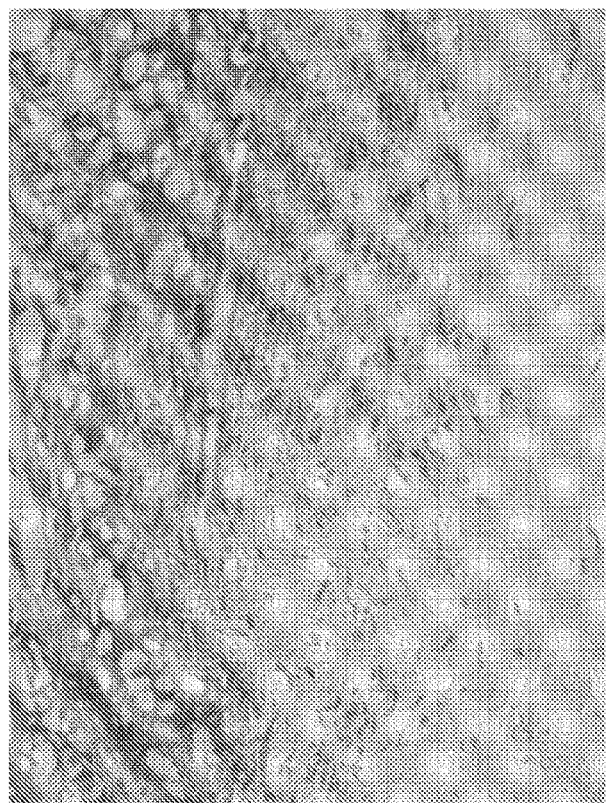
FIGS. 4A-4D include micrographs of tissue with respect to a fibrous implant.
Figure 4A:
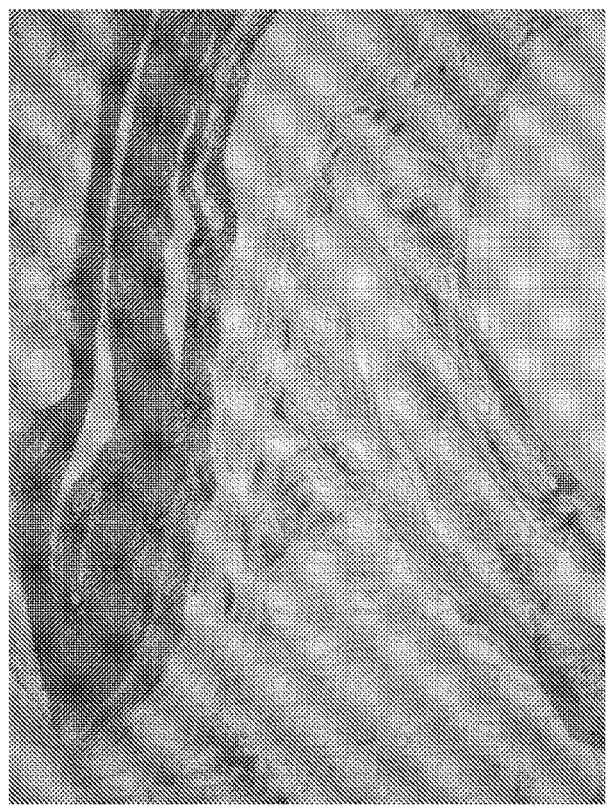
Figure 4D:
Figure 4C:
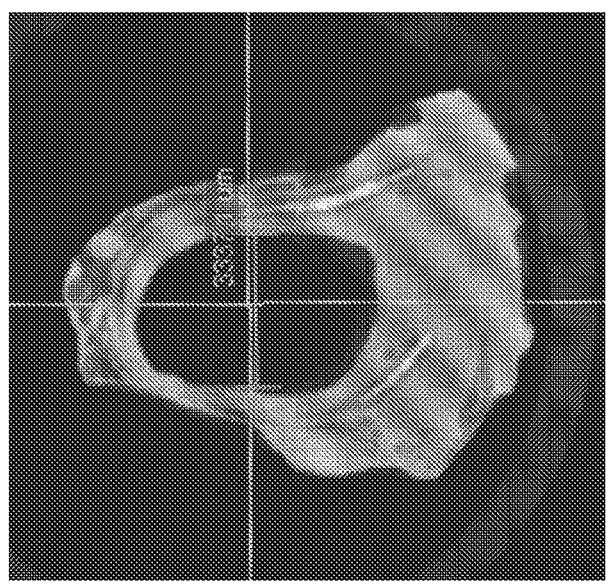

FIG. 4A shows H&E stain for PCL only fibers, which shows cell infiltration from both sides. FIG. 4B shows Collagen II IHC for a trilayer scaffold without growth factors (GFs). FIG. 4C is a microCT of a trilayer scaffold with GFs, which show the open airway and regenerated defect (arrow). FIG. 4D shows collagen II IHC for gradient scaffold with GFs, which shows complete coverage of cartilage-like tissue (collagen II IHC, brown/red color—grey in grayscale) on the outside of the PCL (black) here, and normal ciliated epithelium lining the lumen of the scaffold in all groups. Particularly, FIG. 4A shows the feasibility of the fibrous implant, and shows cell infiltration with electrospun PCL scaffolds after 7 weeks. Additional studies were done for 6 weeks, which include the data of: FIG. 4B shows the trilayer fibrous implant (e.g., PLGA-PCL-PLGA) scaffolds without growth factors; the trilayer scaffolds with growth factors (TGF-$\beta_3$ encapsulated in the outer PLGA layer and EGF in the inner layer) in FIG. 4C; and gradient scaffolds with growth factors in FIG. 4D. The data shows complete coverage of cartilage-like tissue (collagen ii immunostaining) and ciliated epithelium with the addition of PLGA and growth factors in FIG. 4D. The microCT scans revealed acceptable narrowing of the trachea through the grafted sections, but not severe stenosis. From gross examination of the tracheas, scaffolds retained their shape and no air leaks or collapse was evident. Tissue sections revealed the presence of PCL and almost complete resorption of PLGA, as expected. As such, the growth factors can be released faster from the PLGA on a shorter time-scale (e.g., about 4 weeks), and for the PLGA to be degraded and replaced by tissue regeneration, while slower degrading PCL (e.g., about 2 years) and bioactive glass can provide structural support to ensure long-term success of the implant.

The fibrous scaffolds used for implantation can have varied properties, from different fibers, such as in different distributions or gradient distributions. The fibrous scaffolds can be modulated in terms of mechanical integrity, porosity, degradation profiles, and growth factor release profiles and bioactivity. Table 1 provides some examples of variations in the fibers and fibrous scaffold.

In one embodiment, the electrospun fibrous implant can be substantially devoid of pores or opening from the outer wall to luminal wall. Regarding porosity, the lower porosities associated with aligned electrospun fibers are advantageous for tracheal regeneration as a means to maintain an airtight scaffold.

The fibrous implant can be configured to provide desirable contraction, agent release profiles, mechanical integrity, and/or degradation. The variables that can be modulated can include: fibers that include collagen, poly(L-lactide-co-caprolactone), or other similar materials in place of or blended in with PLGA and/or PCL, 2); modified bioactive glass composition (Table 3) or dimensions; a fiber bilayer; growth factors adsorbed or immobilized to the surface of the fibers, coaxially electrospun into the center of the fibers, or growth-factor-loaded microparticles could be encapsulated into the fibers; polymeric layer thickness can be modified; degradation rates of the polymers can be easily altered by changing the intrinsic viscosity (i.e., changing the molecular weight) or by changing the lactic acid to glycolic acid ratio in the PLGA; bioactive glass degradation rate can be controlled by altering the composition; and excipients can be included for growth factor stabilization, including magnesium hydroxide, sucrose, PF-127, trehalose, polyethylene glycol, magnesium carbonate, cyclodextrins, or the like. Table 2 shows variations of the types of fibers, growth factors, and/or cells that can be used in the scaffolds. Table 3 shows variations in the bioactive glass compositions that can be used, with 13-93 being preferred with 13-93B3 being second preferred.

TABLE 1

| Group | Material Gradient? | Growth Factors? | Glass? | Layer Thicknesses§ (mm) |
|---|---|---|---|---|
| Single-layer PCL | N/A | No | No | PCL = 1.0 |
| Single-layer PCL + Glass | N/A | No | Yes | PCL = 1.0 |
| Tri-layer PLGA/PCL/PLGA | No | No | No | PLGA/PCL/PLGA = 0.50/1.00/0.50 |
| Tri-layer + GFs PLGA + EGF/PCL/PLGA + TGF-$\beta_3$ | No | Yes | No | PLGA/PCL/PLGA = 0.50/1.00/0.50 |
| Gradient* PLGA/gradient/PCL/gradient/PLGA | Yes | No | No | PLGA/gradient/PCL/gradient/PLGA = 0.25/0.50/0.50/0.50/0.25 |
| Gradient* + GFs PLGA + EGF/gradient/PCL/gradient/PLGA + TGF-$\beta_3$ | Yes | Yes | No | PLGA/gradient/PCL/gradient/PLGA = 0.25/0.50/0.50/0.50/0.25 |

TABLE 1-continued

| Group | Material Gradient? | Growth Factors? | Glass? | Layer Thicknesses§ (mm) |
|---|---|---|---|---|
| Gradient* + Glass PLGA + EGF/gradient/PCL/ gradient/PLGA + TGF-$\beta_3$ | Yes | Yes | Yes | PLGA/gradient/PCL/gradient/PLGA = 0.25/0.50/0.50/0.50/0.25 |

‡Mechanical testing, degradation, and porosity will be measured only on groups with no gowth factors.
§Layered scaffolds are 2.0 mm in total thickness. Diameter of the aluminum collecting mandrel is 5 mm.
*"Gradient" refers to a gradual, linear transition between layers, as opposed to a sharp interface.

TABLE 2

| Factor | # of levels | Description of levels |
|---|---|---|
| Scaffold Design | 6 | PCL only |
| | | PLGA/PCL/PLGA tri-layer |
| | | PLGA/PCL/PLGA tri-layer + growth factors |
| | | PLGA/PCL/PLGA gradient + growth factors |
| | | PLGA/PCL/PLGA gradient + bioactive glass + growth factors |
| | | PLGA/PCL/PLGA gradient + bioactive glass + growth factors + CS |
| Cell Type | 2 | hBMSCs or hUCMSCs (normal or CFE enriched*) |

TABLE 3

| Glass | SiO$_2$ | B$_2$O$_3$ | Na$_2$O | K$_2$O | MgO | CaO | P$_2$O$_5$ |
|---|---|---|---|---|---|---|---|
| 45S5 | 45.0 | 0 | 24.5 | 0 | 0 | 24.5 | 6.0 |
| 13-93* | 53.0 | 0 | 6.0 | 12.0 | 5.0 | 20.0 | 4.0 |
| 13-93B1 | 35.33 | 17.67 | 6.0 | 12 0 | 5.0 | 20.0 | 4.0 |
| 13-93B3* | 0 | 53.0 | 6.0 | 12.0 | 5.0 | 20.0 | 4.0 |

Figure 6A:
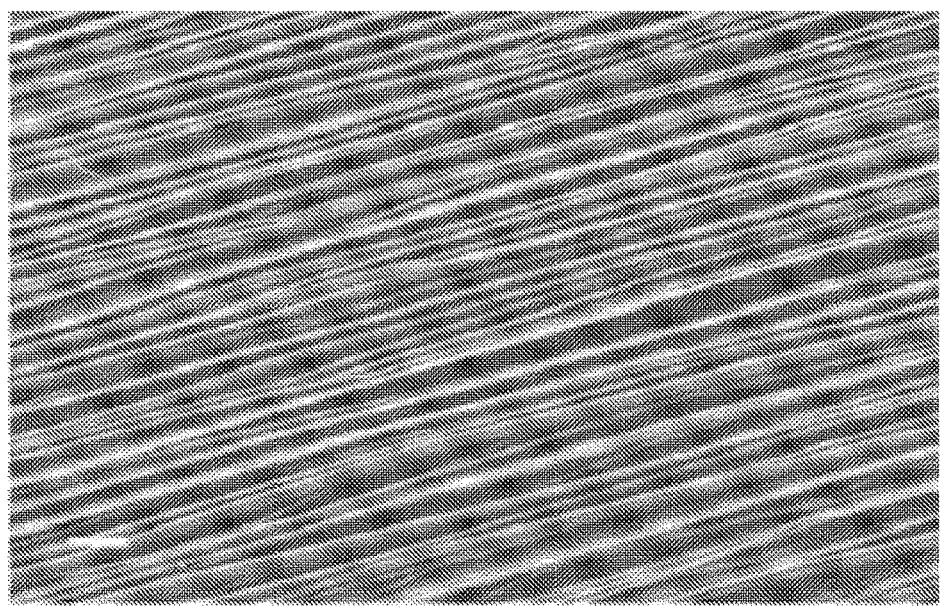
FIG. 6A includes an image of aligned fibers of a fibrous implant patch.
Figure 6B:
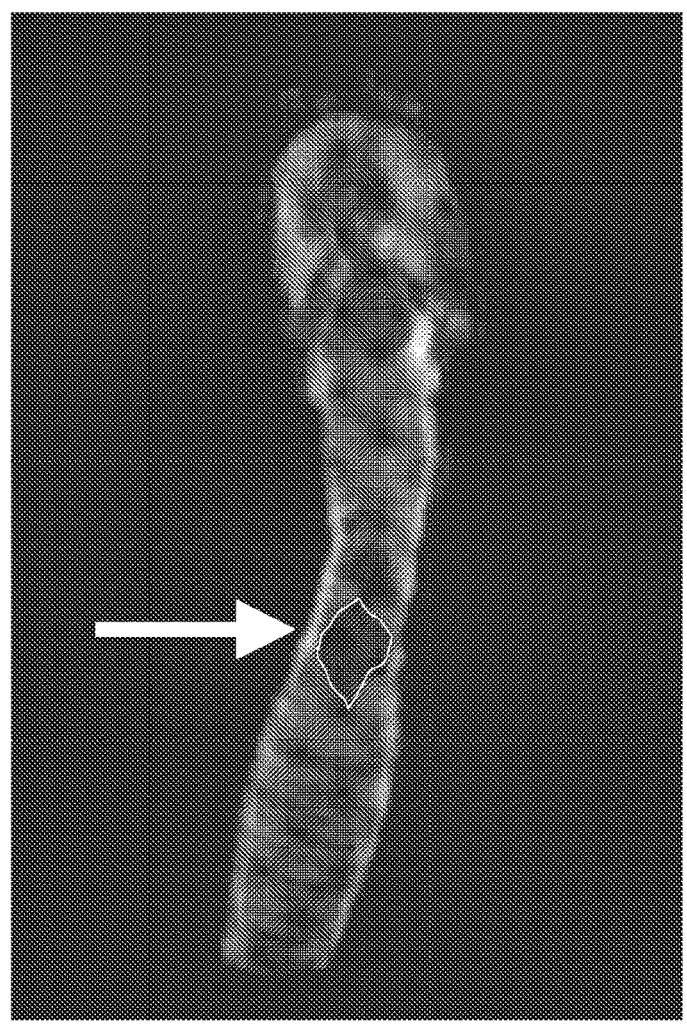
FIG. 6B includes an image of a fibrous implant patch of FIG. 6A implanted into a tracheal defect.

FIGS. 6A-6B show an embodiment of a fibrous implant (FIG. 6A) and implantation thereof (FIG. 6B). The fibrous scaffold was fabricated using a rotating mandrel to create circumferential alignment of electrospun PCL fibers. A high degree of electrospun fiber orientation can provide cell alignment in the direction of fiber orientation. Prior to implantation, the scaffold were imaged with SEM (FIG. 6A). The biomaterial graft was sterilized, and a pre-sized piece was placed over an induced 11) elliptical-shaped defect (FIG. 6B) in the anterior tracheal wall, as well as subcutaneously. After 7 weeks, the rabbits (n=2) were euthanized and the tracheas and subcutaneous implants were collected for analysis. At the conclusion of the study, the tracheas were prepared and sectioned for histological staining (H&E) after being imaged using computer tomographic (CT) imaging. Prior to implantation, scaffolds exhibited fiber alignment (FIG. 6A). During the 7 weeks in vivo, the animals ate and breathed normally with no complications. From gross examination of the tracheas after week 7, the constructs appeared to be covered with vascularized tissue and no air leaks or collapse were evident. The CT scans revealed slight narrowing of the trachea through the grafted sections (FIG. 6B), but no severe stenosis. Sections of the tissue revealed the presence of PCL as expected, and cell infiltration into the scaffold. Based on these preliminary results, we have established that these scaffolds were biocompatible and were rigid enough to keep the trachea patent. The scaffold maintained its shape and minimal degradation of the scaffold material was observed. After implanting manufactured PCL scaffolds into elliptical-shaped defects in rabbit tracheas for 7 weeks, the scaffolds maintained a robust, airtight trachea free of any breathing distress, and exhibited evidence of cell infiltration into the scaffold and tissue regeneration.

Figure 7A:
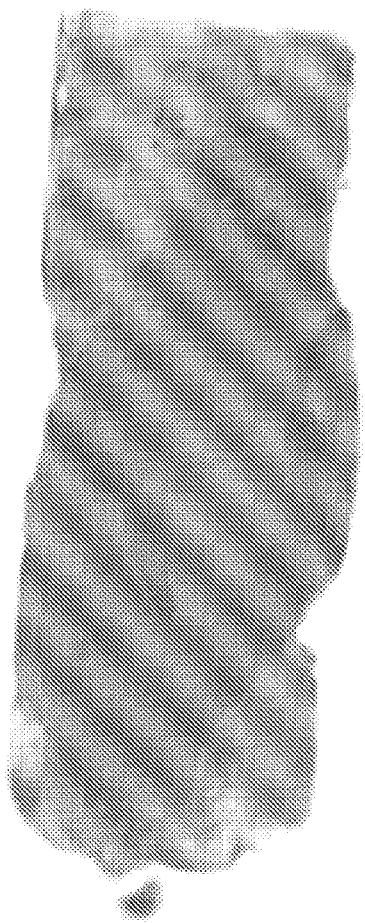
FIG. 7A includes a 3D rendering from microCT analysis of a fibrous implant patch after six weeks in a rabbit trachea (anterior view).
Figure 7B:
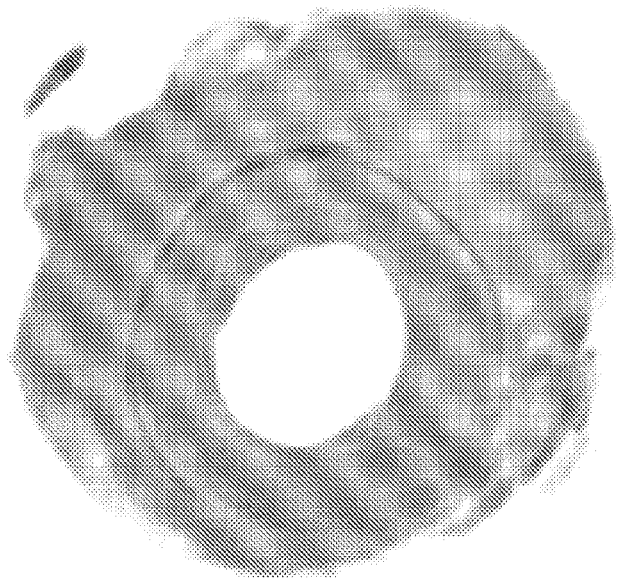
FIG. 7B includes a 3D rendering from microCT analysis of a fibrous implant patch after six weeks in a rabbit trachea (lumen view). Image demonstrates patch's ability to keep airway open.
Figure 7C:
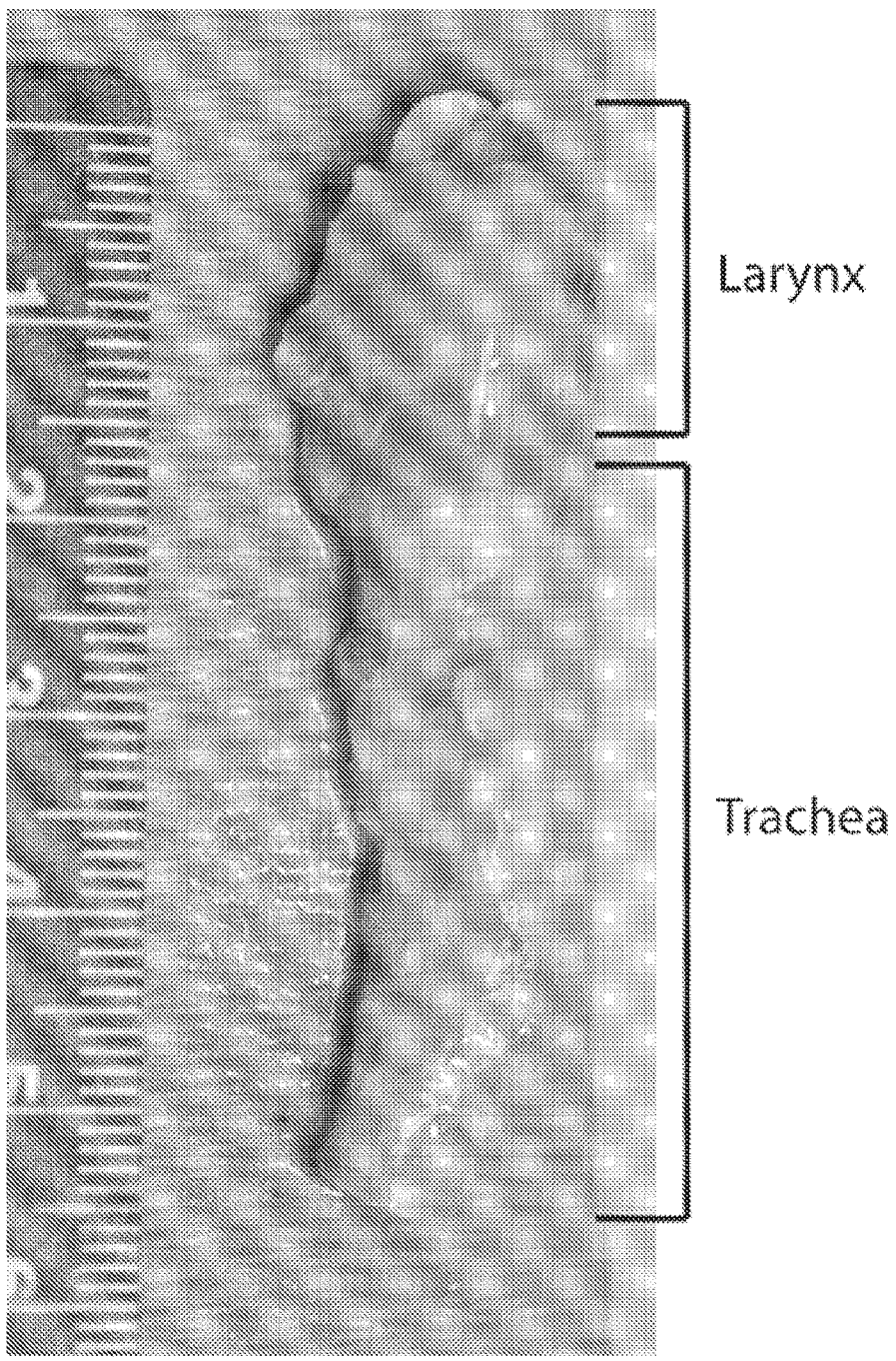
FIG. 7C includes a photographic image of fibrous implant patch after six weeks in a rabbit trachea.

FIG. 7A-7C show results of fibrous implant patch in rabbit trachea after 6 weeks. FIG. 7A includes a 3D rendering from microCT analysis of a fibrous implant patch after six weeks in a rabbit trachea (anterior view). FIG. 7B includes a 3D rendering from microCT analysis of a fibrous implant patch after six weeks in a rabbit trachea (lumen view). Image demonstrates patch's ability to keep airway open. FIG. 7C includes a photographic image of fibrous implant patch after six weeks in a rabbit trachea. Three experimental groups were fabricated: trilayer [poly(lactic-co-glycolic acid) (PLGA)-polycaprolactone (PCL)-PLGA] scaffolds without growth factors, trilayer scaffolds with growth factors (transforming growth factor-$\beta_3$ encapsulated in the outer PLGA layer and epidermal growth factor in the inner layer), and gradient scaffolds with growth factors. The scaffolds were fabricated using a rotating mandrel to create aligned electrospun fibers. Prior to implantation, scaffolds were imaged with SEM. The biomaterial grafts were sterilized, and pre-sized pieces were placed over an induced elliptical-shaped defect in the anterior tracheal wall of New Zealand White rabbits (two rabbits per group, six rabbits total). After 6 weeks, the rabbits were euthanized and the tracheas and subcutaneous implants were collected for analysis. At the conclusion of the study, the tracheas were prepared and sectioned for histological and immunohistochemical staining after being imaged using microCT imaging. During our 6 week in vivo study, the rabbits ate and breathed normally with no complications. None of the rabbits had any obvious stridor. The microCT scans revealed minimal narrowing of the trachea through the grafted sections, but not severe stenosis. From gross examination and microCT analysis of the tracheas, scaffolds retained their shape and no air leaks or collapse were evident (FIG. 7A-C). After implanting manufactured scaffolds into elliptical-shaped defects in rabbit tracheas for 6 weeks, the scaffolds maintained a robust, airtight trachea allowing the animals to be free of any breathing distress. The implanted material exhibited evidence of cell infiltration into the scaffold, tissue regeneration, and re-epithelialization of the lumen.

Based on the results, we have established that these fibrous scaffolds are biocompatible and are rigid enough to keep the trachea patent. The scaffold maintained its shape and minimal degradation of the scaffold material was observed. Because of PCL's slow degradation profile, a faster degrading alternative to PCL, such as PLGA can be used to allow tissue in-growth, while not compromising the mechanical stability of the construct. Two types of fibers can be prepared into a scaffold having a gradient of PLGA and PCL. The co-electrospinning process, with two or more syringes and power supplies, can be used to create multi-component fibrous scaffolds.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A fibrous scaffold consisting of:
a layer comprising:
a first type of polymeric electrospun fiber; and
a second type of polymeric electrospun fiber;
wherein at least one of the first type of polymeric electrospun fiber and the second type of polymeric electrospun fiber comprise a polymer selected from the group consisting of polyglycolic acid, polylactic acid, poly(lactic-co-glycolic acid), poly(L-lactide-co-caprolactone), and polycaprolactone; and
wherein the first type of polymeric electrospun fiber and the second type of polymeric electrospun fiber are co-electrospun;
wherein the first type of polymeric electrospun fiber and the second type of polymeric electrospun fiber are randomly oriented;
wherein the fibrous scaffold has a shape selected from the group consisting of a patch and a sheet.

2. The fibrous scaffold of claim 1, wherein the first type of polymeric electrospun fiber comprises polyglycolic acid, and wherein the second type of polymeric electrospun fiber comprises poly(L-lactide-co-caprolactone).

3. The fibrous scaffold of claim 1, wherein the first type of polymeric electrospun fiber comprises poly(lactic-co-glycolic acid), and wherein the second type of polymeric electrospun fiber comprises a biodegradable polymer.

4. The fibrous scaffold of claim 1, wherein the first type of polymeric electrospun fiber comprises polycaprolactone, and wherein the second type of polymeric electrospun fiber comprises poly(lactic-co-glycolic acid).

5. The fibrous scaffold of claim 1, wherein the fibrous scaffold is configured for use with a wound.

6. The fibrous scaffold of claim 1, wherein at least one of the first type of polymeric electrospun fiber and the second type of polymer electrospun fiber further comprise an active agent.

7. The fibrous scaffold of claim 6, wherein the active agent is selected from the group consisting of an antimicrobial, a pharmaceutical, a tissue growth factor, a protein, a nanophase material, and combinations thereof.

8. The fibrous scaffold of claim 1, wherein the first type of polymeric electrospun fiber comprises a first active agent, and wherein the second type of polymeric electrospun fiber comprises a second active agent different from the first active agent.

9. The fibrous scaffold of claim 1, further comprising a plurality of live cells.

* * * * *